United States Patent [19]
Whisson

[11] Patent Number: 5,680,110
[45] Date of Patent: Oct. 21, 1997

[54] BLOOD DONATION MONITORING MEANS FOR MONITORING THE FLOW OF BLOOD THROUGH A RECEPTACLE

[75] Inventor: Maxwell Edmund Whisson, Nedlands, Australia

[73] Assignee: Max-Medical Pty Ltd., Nedlands, Australia

[21] Appl. No.: 591,462

[22] PCT Filed: Aug. 5, 1994

[86] PCT No.: PCT/AU94/00450

§ 371 Date: Apr. 4, 1996

§ 102(e) Date: Apr. 4, 1996

[87] PCT Pub. No.: WO95/04557

PCT Pub. Date: Feb. 16, 1995

[30] Foreign Application Priority Data

Aug. 5, 1993 [AU] Australia .................. PM0419

[51] Int. Cl.⁶ ........................................ G08B 21/00
[52] U.S. Cl. ...................... 340/613; 340/606; 177/118
[58] Field of Search ........................ 340/613, 606, 340/618, 603; 177/118; 128/DIG. 13

[56] References Cited

U.S. PATENT DOCUMENTS 5,010,968  4/1991  Barrow ..................... 177/118
5,371,329 12/1994 Fillaud .................. 128/DIG. 13

*Primary Examiner*—Jeffery Hofsass
*Assistant Examiner*—Anh La
*Attorney, Agent, or Firm*—Merchant, Gould, Smith, Edell, Welter & Schmidt, P.A.

[57] ABSTRACT

A blood donation monitoring means comprising a support platform (12), being rockably supported by a support (18), a drive means (37, 39, 40) supported operatively connected to the support platform (12) to cause a rocking of the support platform (12), a weight sensing means (23) associated with the support for the support platform, a flow line support (16) adapted to receive a flow line for a receptacle to be supported on the support platform (12), the flow line support (16) including a flow control means (42) to control the flow through the control line, a control means operatively connected to the flow control means (16) and having an input from the weight sensing means (23), said control means having a monitoring means which is adapted to monitor the rate of change of weight of the contents of the support platform (12) and activate the flow control means (16) in accordance with the weight changes of the contents of the support platform (12) and ensure delivery of a predetermined quantity of blood to the receptacle through the flow line.

17 Claims, 4 Drawing Sheets

5,680,110

BLOOD DONATION MONITORING MEANS FOR MONITORING THE FLOW OF BLOOD THROUGH A RECEPTACLE

This invention relates to a blood flow monitoring device which can be used for monitoring the delivery of blood from a blood donor.

Accordingly, the invention resides in a blood donation monitoring means comprising; a support platform roackably supported by a support; a drive means supported from the support and operatively connected to the support platform to cause joint pivotal movement of the support platform about two axes; a weight sensing means associated with the support for the support platform; a display adapted to display a value representative of the quantity of blood in the receptacle determined from the output of the weight sensing means; a flow line support adapted to receive a flow line from a receptacle to be supported on the support platform, said flow line support including a flow control means to control the flow through the flow line to the receptacle; a control means operatively connected to the flow control means; said control means being adapted to periodically derive an input from the weight sensing means and monitor the rate of change of weight of the contents of the support platform; said control means being adapted to activate the flow control means to close the flow line on delivery of a predetermined quantity of blood to the receptacle through the flow lines; and wherein the control means is further adapted not to activate the flow control means on detecting a variation in weight sensed by the weighing means which is contrary to expected variations, said control means being adapted to cause the display to display a signal indicative of the presence of an unexpected variation in weight.

According to a preferred feature of the invention the predetermined amount of blood can be varied from collection to collection.

According to a preferred feature of the invention the drive means and control circuit is driven from an electrical power supply comprising a set of electrolytic storage cells associated with a set of photovoltaic cells and a charging circuit.

According to a preferred feature the control means is adapted to periodically activate the drive means and said control means is adapted to measure the weight of the contents of the support platform when the drive means is deactivated and determine the change in weight from the earlier measurement.

According to a preferred feature of the previous feature the display indicates visual and/or audio display indicative of the ratio of the amount of blood collected to the predetermined amount to be collected.

The invention will be more fully understood in the light of the following description of one specific embodiment. The description is made with reference to the accompanying drawings of which:

Figure 1:
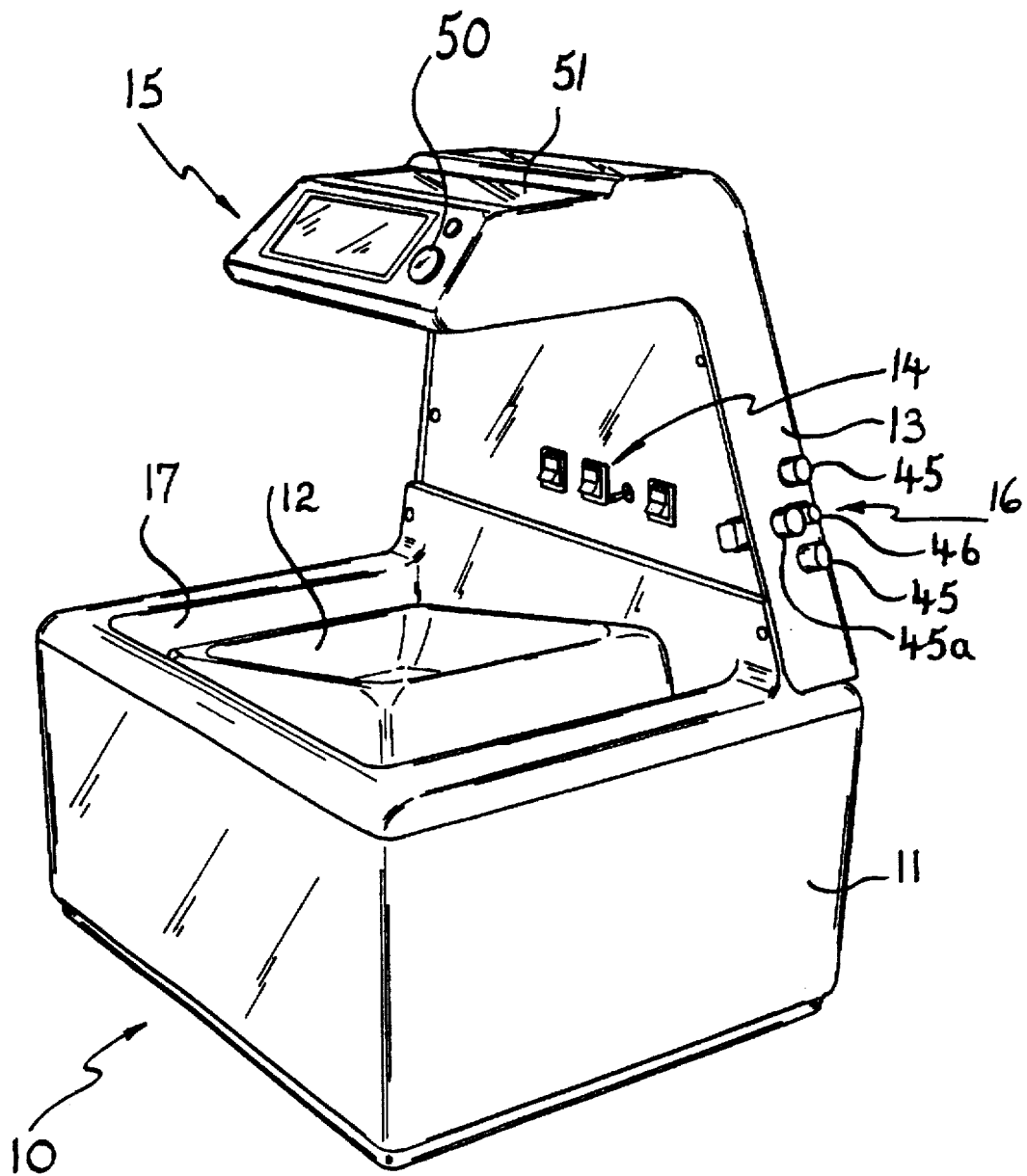
FIG. 1 is an isometric view of a blood collection monitoring apparatus according to the embodiment.
Figure 2:
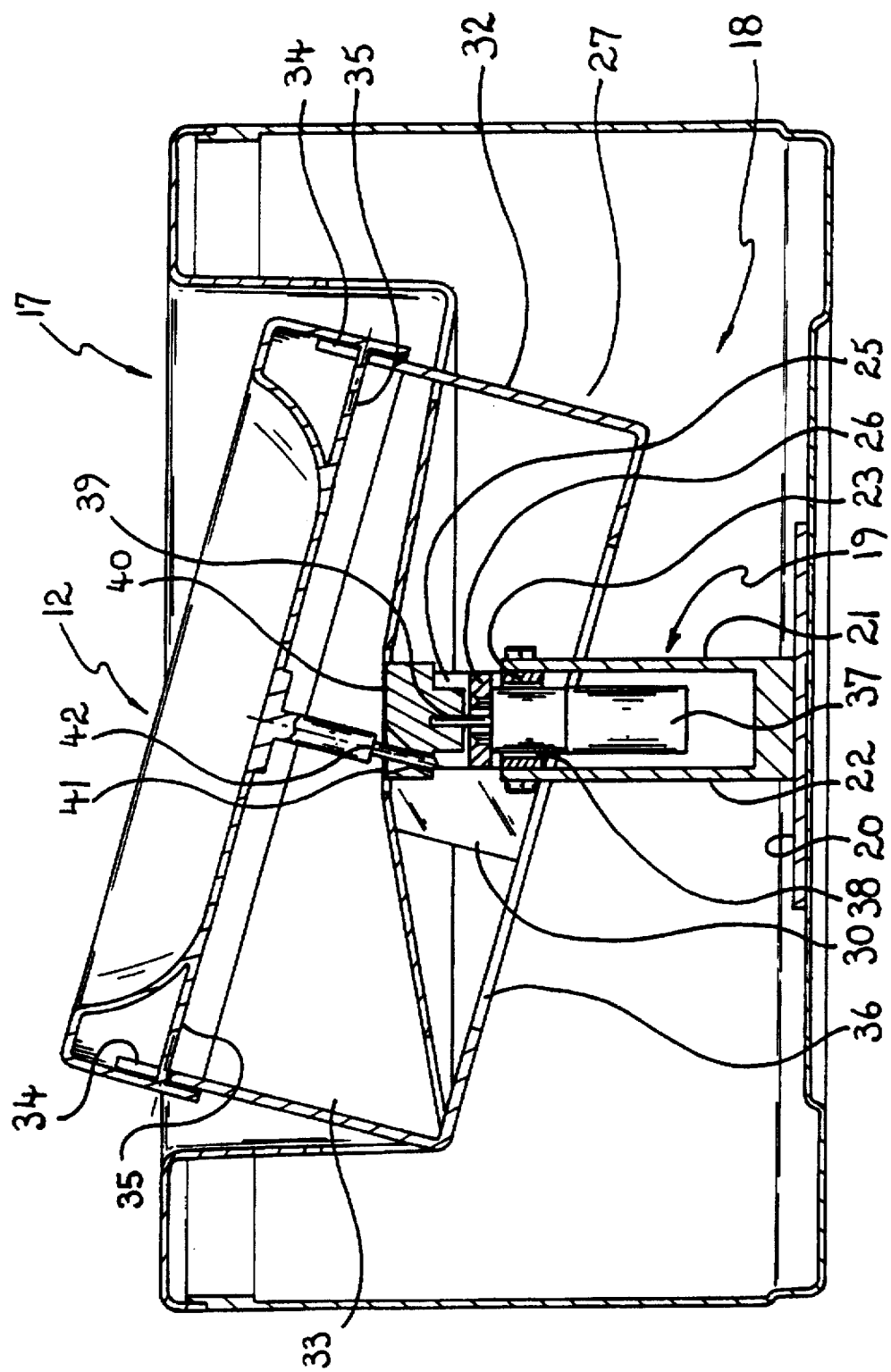
FIG. 2 is a sectional side elevation of the base portion of the embodiment.

The embodiment is directed towards a device which can be used for the collection of blood and monitoring such collection.

The embodiment comprises a housing 10 having a lower portion 11 which accommodates a support tray 12 and a drive means for causing reciprocation of the tray. The housing further comprises a upper portion 13 which extends upwardly from one side of the base 11 and accommodates an appropriate control switch 14, a display 15, and flow line support 16. Both the lower and upper portion 11 and 13 accommodate the control circuitry for the device.

The upper portion 13 comprises an upstanding wall supported from the rear of the lower portion 11. The top of the wall supports a substantially horizontal portion which accommodates the control circuitry, control switches and display panels. The horizontal portion generally overlies the support tray and has an area similar to the area of the upper face of the lower portion.

The lower portion 11 is essentially cubic in configuration and is provided with an open upper face 17. The support tray 12 is configured such that it is received within the upper face 17 and is supported able to be caused to pivot about two substantially horizontal perpendicular axes in the open face 17. The tray 12 is formed with an upper face which is recessed in a manner such that it will support a blood collection bag and will prevent substantial movement of the bag on the tray as a result of the cyclic tilting action of the tray.

Figure 3:
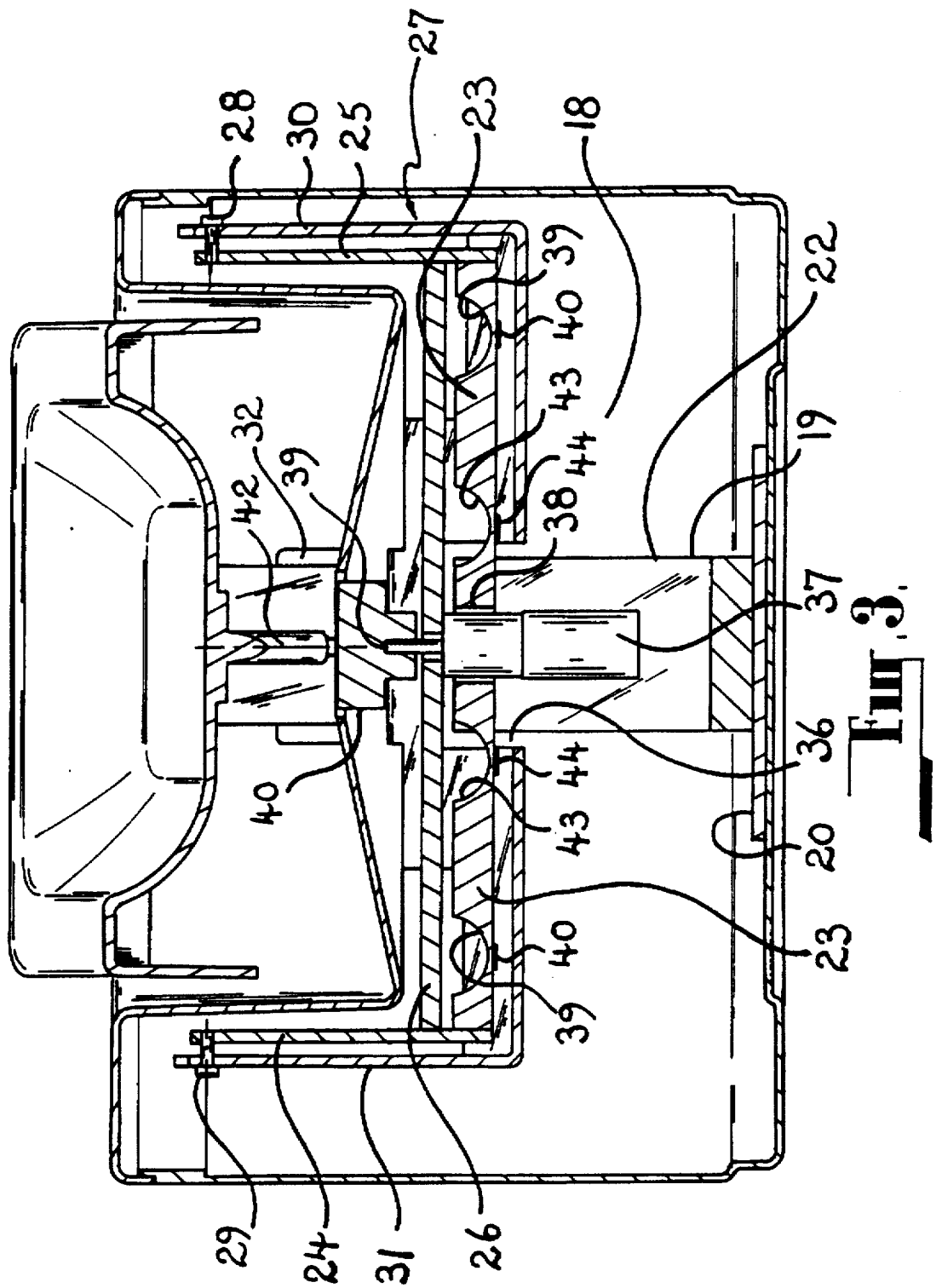
FIG. 3 is a sectional end elevation of the base according to the embodiment.
Figure 4:
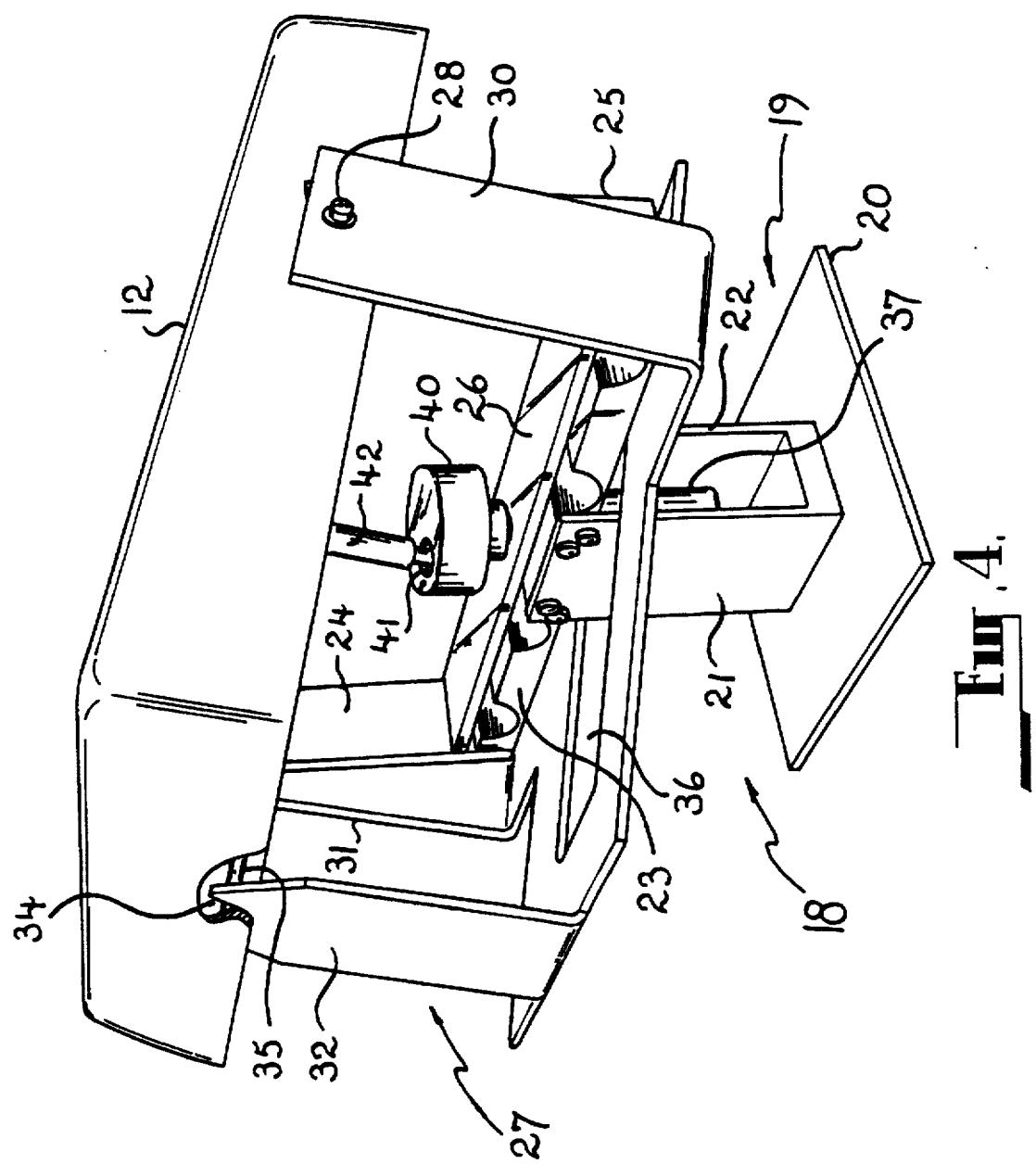
FIG. 4 is an isometric view of the tray support of the embodiment.

The support tray 12 is supported within the base 11 from a support structure 18 (see FIG. 3) which has a base 19 defined by a lower plate 20 which is adapted to be fixed to the bottom wall of the lower portion 11 of the housing. The base has an upstanding pair of parallel webs 21 and 22. The upper ends of the webs 21 and 22 support the central portion of a beam 23 which extends to each side of the space between the webs 21 and 22 and which supports an upright 24 and 25 at each end. The uprights 24 and 25 are further interconnected by a secondary beam 26 which lies parallel to the primary beam 23 and is spaced upwardly therefrom.

The upper end of each of the uprights 24 and 25 pivotally supports a support frame 27 through pivots 28 and 29 where the pivot axis between the pivots 28 and 29 is substantially horizontal.

The support frame 27 is of a generally cruciform configuration where the end of each arm is formed with an upwardly extending portion which provides two pairs of upwardly extending arms. The arms of each pair of arms are opposite each other and the axes interconnecting the pairs of arms are substantially perpendicular. One pair of upwardly extending arms 30 and 31 are pivotally mounted to the uprights 24 and 25 through the pivots 28 and 29 respectively to be pivotally supported from the base element 19 about the axis between the pivots 28 and 29. The other pair of upwardly extending arms 32 and 33 are each formed with a V-shaped recess 34 which each pivotally receive a pivot pin or shaft 35 provided on the underneath the tray 12 towards each end thereof such that the tray is pivotally supported between the second pair of upwardly projecting arms 32 and 33 for pivotable movement about the axis of the shaft 35.

The central portion of the support frame which accommodates the second pair of upwardly extending arms 32 and 33 is formed with a slot shaped aperture 36 which has a width greater than to the width of the webs 21 and 22 and which enables the support frame 27 to pivot over the base about the pivots 28 and 29.

The base 19 also supports a drive motor 37 which is supported from the secondary beam 26 to depend downwardly therefrom but which is received within an opening 38 provided in the primary beam 23 such that it does not interfere with and is not supported in any way, by the primary beam 23. The drive motor 37 is provided with an upwardly extending drive shaft 39 which has a wheel 40 mounted to its upper end. The wheel 40 is formed in its upper surface with a socket 41 at a position offset from the central axis of the wheel 40 and the shaft 39. If desired the wheel can be replaced by a crank or like device.

The underneath of the tray 12 is provided with a downwardly depending shaft 42 which is formed at its lower end with a ball-shaped element (not shown) which is pivotally received within the socket 41. The shaft 42 is located centrally on the tray 12. On rotation of the wheel 40 as a result of the activation of the drive motor 37 the free end of the downwardly extending shaft 42 is caused to orbit around the central axis of the shaft and wheel and as a result the tray 12 is caused to pivot about the central axis of the shaft 35 between the second pair of upwardly extending arms 32 and 33 and the axis between the pivots 28 and 29 provided between the uprights 24 and 25 on the base 19. This joint cyclic tilting of the tray 12 about a pair of substantially perpendicular axes provides an action which facilitates the rapid and consistent mixing of blood and anticoagulant within a bag which is supported on the tray 12.

The operation of the drive motor through the control circuit is such that each time the drive motor stops the wheel and thus the tray is at the same position. This is facilitated by the presence of a magnet (not shown) mounted to the wheel 40 which is associated with a Hall effect sensor (not shown) provided on the secondary beam 26 to enable the control circuit to always stop the drive motor 37 with the tray in the same position. In use a receptacle is placed on the tray such that the inlet is lowermost. As a result blood entering the receptacle must flow through the anticoagulant accommodated within the receptacle when the tray is stationary.

The mounting and construction of the tray is such that it can be readily lifted out of engagement with the recesses 34 on the arms 32 and 33 of the support frame 27 and out of engagement with the wheel for the tray to be cleaned. When cleaned the tray is readily capable of being re-engaged with the support 27 and the wheel.

It has been found that the repetitive tilting of the tray about two axes, as a result of the construction according to the embodiment, enables the blood, collected during a normal six minute donation period, to be rapidly mixed with the anticoagulant contained within the receiving bag with little segregation of the constituents of the blood, such as accumulation of red blood cells which has been a common difficulty with mechanisms used in the past.

The primary beam 23 of the base provides the primary support for the tray, its contents and the support frame 27 from the base 19. The primary beam 23 is supported symmetrically from the webs 21 and 22 and also symmetrically supports the tray 12 and its contents. The beam is formed with a set of four symmetrically located transverse grooves 43 and each groove is associated with a strain gauge 44. The strain gauges are interconnected to an electrical circuit which is able to provide a measure indicative of the weight of the tray and its contents. In addition the control circuitry is able to provide a display representative of the weight of the contents of the bag in the tray and the rate of change of the weight of the contents of the tray. The configuration and construction of the primary beam may take any desirable form to facilitate the symmetrical support and use of four strain gauges to provide a measure representative of weight.

In operation the drive motor 37 is activated intermittently whereby during each rest period the weight as sensed by the strain gauges 44, is measured and the change in weight since the previous rest period is determined.

The support arrangement for the tray according to the embodiment as described above comprises a means whereby the pivotal support for the tray and the drive for causing such pivotal movement of the tray is carried from a common carriage which is in turn supported symmetrically from the base element whereby the nature of the support provided for the carriage enables the weight of the tray and support carriage and the contents of the tray to be accurately monitored, to ensure accurate monitoring of the contents of the tray 12.

The upper portion 13 of the housing is provided with a flow line support 16 which comprises a set of three upwardly fixed extending spigots 45 and a fourth movable spigot 46. The fixed spigots 45 together form a triangular array of spigots. The movable spigot 46 is capable of moving towards the central spigot 45a. In use a blood flow line is laced between the movable spigot 46 and the three fixed spigots 45. The movable spigot 46 is associated with a latch means which is activated by a solenoid or like device which on activation will caused the movable spigot 46 to move towards the fixed spigots 45 whereby the flow line is clamped to prevent flow of blood through that line.

The control of the flow line support means 16 is effected from the control circuit accommodated within the upper portion 13 of the housing to control the flow of blood to the receptacle carried on the tray 12.

The control circuit incorporates a main control switch 50 to initiate the operation of the device. In addition the control circuit is provided with a micro processor which in association with the display 15 provides a set of instructions to the operator and which incorporates a monitoring means which can control the flow line support in association with those instructions. The control circuit is further provided with appropriate toggle switches 14 and memory circuitry which enable a value for a predetermined volume of blood which is to be collected to be introduced into the memory of the control circuit such that on that volume having been collected the flow line support will be activated to prevent any further flow of blood to the receptacle. On first use of the device the volume or weight of blood to be collected is stored into the memory. This can be varied from time to time but the memory will retain the figure previously entered until it is subsequently changed.

The control circuit is also able to provide a display of the amount of blood collected by indicating the weight of blood collected or the volume of the blood collected. In providing such the circuit operates on the measure derived from the weight sensing circuit to provide a measure of the volume. If desired a suitable switch may be provided with the display to be able to change the display from indicating weight to indicate volume during operation of the device.

The display provides a multiple of displays. One form of display provides an accurate digital display of the volume and/or weight of blood in the collection bag and the time elapsed since the collection of blood commenced. The other form of display comprises an array of lights which are activated sequentially whereby at the commencement of collection no lights are activated and at the termination of collection when the predetermined volume of blood has been collected (irrespective of that amount) all of the lights are lit. As a result the array of lights enable a ready determination to be made of the percentage of the amount to be collected which has actually been received in the collection bag. The display can also provide a periodic audio signal indicative of the percentage of the collection that has been received. This may comprise a variable signal which varies in pitch and frequency throughout the collection period.

At the commencement of the use of the apparatus it is switched on and the user is instructed by the display to locate a collection bag on the tray. Only after a collection bag is located on the tray 12 will the apparatus proceed to the next step at which the display is set to indicate zero in relation to both the weight and/or volume, of blood in the collection bag. The sensing of the presence of a collection bag in the tray may be effected by sensing the increased weight of the tray due to the presence of the collection bag or by means of a light sensation cell located on the tray. The flow line to the collection bag is then installed in the flow line support 16 and is connected to a donor. When the receptacle and flow line are in position blood begins to flow to the receptacle and on an initial quantity of blood (e.g. 10 grams) being received the control circuit activates the drive motor 37 to cause the cyclic tilting of the tray 12 about its pivot axes. Such activation of the motor is intermittent and is for a period of several rotations of the wheel. During each rest phase the weight of the tray and the receptacle is measured. The monitoring means of the control circuit then compares the weight currently being measured with the weight previously measured and provides an indication at the display of the current weight of the contents of the tray.

If desired the display can also provide an indication of the flow rate which is derived from the change in weight of the contents of the tray between the current measurement and the previous measurement. In the event of the flow rate not being within a satisfactory range a further display is provided and the display is associated with a suitable audible alarm to draw the attention of the operator to the low flow rate in order that the matter can be rectified. After intervention by the operator the operator may press the main control switch 50 again whereon the control circuit will enable the display to continue as if the interruption had not occurred.

In addition, the control circuit is such that it will not accept any spurious indicators of mass or volume of the contents of the receptacle which is contrary to the expected flow rate from a donor. Such a circumstance can arise when an operator taps or touches the receptacle which results in an excessive weight being measured by the control circuit or when an operator removes the bag from the tray during collection for inspection or labelling and then replaces the bag. In such circumstances the weight measured is not representative of the actual weight of the contents of the tray and the variation in weight is not representative. This rapid weight increase or decrease would be beyond that which one would normally expect from a blood donor. The monitoring means in the form of the microprocessor is programmed not to accept any measurements which are beyond the normal flow rates expected of a donor and which are not representative of the actual flow rate to the bag. Therefore the control circuit ignores any spurious weight indicators that may result from the receptacle being inadvertently knocked or tapped, and will not shut off the blood flow in the event of such an incident. The monitoring means however does provide a signal indicating an abnormal condition which in the above circumstances would be readily apparent or would be rectified very shortly on resumption of normal conditions.

The upper portion of the housing is also provided with a set of photovoltaic cells 51 which are associated with a set of electrolytic storage batteries and a charging circuit. These enable the device to be portable and capable of being independent of a mains power supply.

The control circuit also includes a Calibration programme whereby the weighing sensor may be calibrated. The programme provides a sequence of instructions on the display. The instructions require the operator to locate a set of standard weights (e.g. 10 g, 20 g, 30 g weights sequentially) on the tray and on location of each weight the circuit calibrates the sensor. This Calibration programme can be initiated at any time the device is not in collection mode.

It should be appreciated that the scope of the present invention need not be limited to the particular scope of the embodiment described above.

The claims defining the invention are as follows:
I claim:

1. A blood donation monitoring means comprising; a support platform roackably supported by a support; a drive means supported from the support and operatively connected to the support platform to cause joint pivotal movement of the support platform about two axes; a weight sensing means associated with the support for the support platform; a display adapted to display a value representative of the quantity of blood in the receptacle determined from the output of the weight sensing means; a flow line support adapted to receive a flow line from a receptacle to be supported on the support platform, said flow line support including a flow control means to control the flow through the flow line to the receptacle; a control means operatively connected to the flow control means; said control means being adapted to periodically derive an input from the weight sensing means and monitor the rate of change of weight of the contents of the support platform; said control means being adapted to activate the flow control means to close the flow line on delivery of a predetermined quantity of blood to the receptacle through the flow lines; and wherein the control means is further adapted not to activate the flow control means on detecting a variation in weight sensed by the weighing means which is contrary to expected variations, said control means being adapted to cause the display to display a signal indicative of the presence of an unexpected variation in weight.

2. A blood donation means as claimed at claims 1 wherein the control means can be adjusted in order that the predetermined quantity of blood can be varied.

3. A blood donation means as claimed at claim 1 wherein the control means is adapted to periodically activate the drive means and said control means is adapted to measure the weight of the contents of the support platform when the drive means is deactivated and determine the change in weight from the earlier measurement.

4. A blood donation monitoring means as claimed at claim 1 wherein the display means includes a signalling means adapted to provide a signal indicative of the weight of the contents of the support platform.

5. A blood donation monitoring means as claimed at claim 4 wherein the signal varies with the variation of weight of the contents of the support platform.

6. A blood donation monitoring means as claimed at claim 4 wherein the signal comprises an audible signal.

7. A blood donation monitoring means as claimed at claims 4 wherein the signalling means comprises an illumination means.

8. A blood monitoring means as claimed at claim 1 wherein the drive means, weighing sensing means, control means and flow control means is powered from an electrical power supply comprising a battery of electrolytic cells.

9. A blood donation monitoring means as claimed at claim 8 wherein the battery is associated with a charging circuit.

10. A blood donation monitoring means as claimed at claim 9 wherein the charging circuit is connected to a set of photovoltaic cells.

11. A blood donation monitoring means as claimed at claim 1 further comprising a lower housing which accommodates the support, the support platform and drive means and where the support platform is received in an opening provided in the upper face of the lower housing; and an upper housing supported from the lower housing to lie above the support platform in spaced relation thereto.

12. A blood donation monitoring means as claimed at claim 11 wherein the area of the upper housing is generally similar to the area of the upper face of the lower housing.

13. A blood donation monitoring means as claimed at claim 11 wherein the display and the flow control means is accommodated in the upper housing.

14. A blood donation monitoring means as claimed at claim 3 wherein the display means includes a signalling means adapted to provide a signal indicative of the weight of the contents of the support platform.

15. A blood monitoring means as claimed at claim 4 wherein the drive means, weighing sensing means, control means and flow control means is powered from an electrical power supply comprising a battery of electrolytic cells.

16. A blood monitoring means as claimed at claim 7 wherein the drive means, weighing sensing means, control means and flow control means is powered from an electrical power supply comprising a battery of electrolytic cells.

17. A blood donation monitoring means as claimed at claim 12 wherein the display and the flow control means is accommodated in the upper housing.

* * * * *